United States Patent
Patel et al.

(10) Patent No.: US 10,131,057 B2
(45) Date of Patent: Nov. 20, 2018

(54) ATTACHMENT MECHANISMS FOR STABILZATION OF SUBSEA VEHICLES

(71) Applicant: Saudi Arabian Oil Company, Dhahran (SA)

(72) Inventors: Sahejad Patel, Thuwal (SA); Fadl Abdellatif, Thuwal (SA); Hassane Trigui, Thuwal (SA); Ali Outa, Thuwal (SA); Abdullah Arab, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/623,565

(22) Filed: Jun. 15, 2017

(65) Prior Publication Data
US 2018/0079086 A1    Mar. 22, 2018

Related U.S. Application Data

(60) Provisional application No. 62/397,175, filed on Sep. 20, 2016.

(51) Int. Cl.
*B25J 15/00* (2006.01)
*B63G 8/00* (2006.01)
*F16H 19/08* (2006.01)
*B63H 19/08* (2006.01)

(52) U.S. Cl.
CPC .......... *B25J 15/0028* (2013.01); *B63G 8/001* (2013.01); *F16H 19/08* (2013.01); *B63G 2008/008* (2013.01); *B63H 19/08* (2013.01); *F16H 2019/085* (2013.01)

(58) Field of Classification Search
CPC ... B63G 8/001; B63G 2008/008; B63C 11/52; B63C 11/34; B63H 19/08; B25J 15/0028
USPC .............. 405/188, 190, 191, 184.1; 114/312; 701/21
See application file for complete search history.

(56) References Cited

U.S. PATENT DOCUMENTS 4,034,568 A    7/1977  Mason
4,705,331 A *  11/1987 Britton ................ E02B 17/0026
                                                        24/463

(Continued)

FOREIGN PATENT DOCUMENTS

CN           105922278 A    9/2016
WO    WO 2013/144601 A1    10/2013
WO    WO 2016/120071 A1     8/2016

*Primary Examiner* — Carib A Oquendo
(74) *Attorney, Agent, or Firm* — Leason Ellis LLP

(57) ABSTRACT

Systems and methods for securing a remotely operated vehicle (ROV) to a subsea structure during cleaning, maintenance, or inspection of the structure surface are provided. In one or more embodiments, an attachment mechanism includes a pair of grasping hooks that are raised and lowered when driven by a motorized drive. In one or more embodiments, an attachment mechanism includes a rigid holder having a mechanical stop and connected to a swing arm, the swing arm configured to rotate inward, but not outward beyond the mechanical stop. In one or more embodiments, an attachment mechanism includes a plurality of linked segments in series, each connected at a plurality of pivot points. A pair of wires passes through the plurality of linked segments and connects to a pair of pulleys that extend or retract the wires, thereby rotating the plurality of linked segments.

15 Claims, 6 Drawing Sheets

(56) References Cited

U.S. PATENT DOCUMENTS

| | | | |
|---|---|---|---|
| 4,720,213 A * | 1/1988 | Gernhardt | B63B 59/10 15/104.04 |
| 5,200,679 A | 4/1993 | Graham | |
| 5,273,376 A * | 12/1993 | Ritter, Jr. | E21B 33/038 405/169 |
| 6,481,195 B1 | 11/2002 | Blase | |
| 9,239,297 B2 * | 1/2016 | Sibai | B25J 5/007 |
| 9,285,345 B2 | 3/2016 | Boenisch | |
| 2003/0216092 A1 * | 11/2003 | Dornier, II | B60F 3/0061 440/36 |
| 2010/0318242 A1 * | 12/2010 | Jacobsen | F41H 13/00 701/2 |
| 2016/0272291 A1 * | 9/2016 | Outa | B60F 3/0015 |
| 2018/0079476 A1 * | 3/2018 | Abdellatif | B63G 8/14 |
| 2018/0080905 A1 * | 3/2018 | Al Nahwi | G01N 29/225 |

* cited by examiner

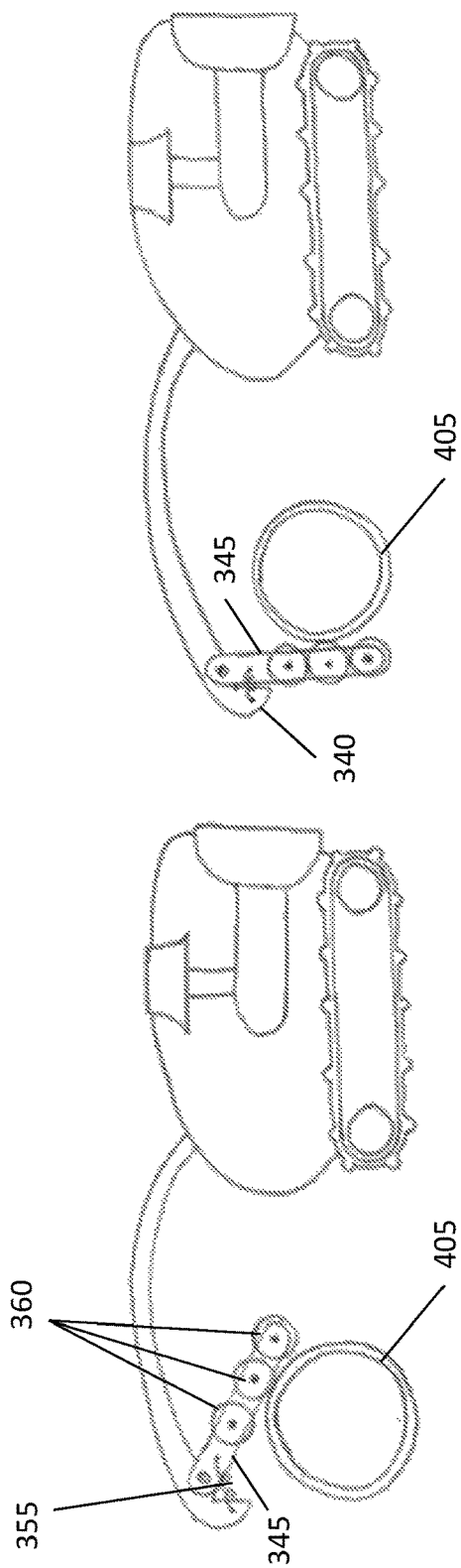

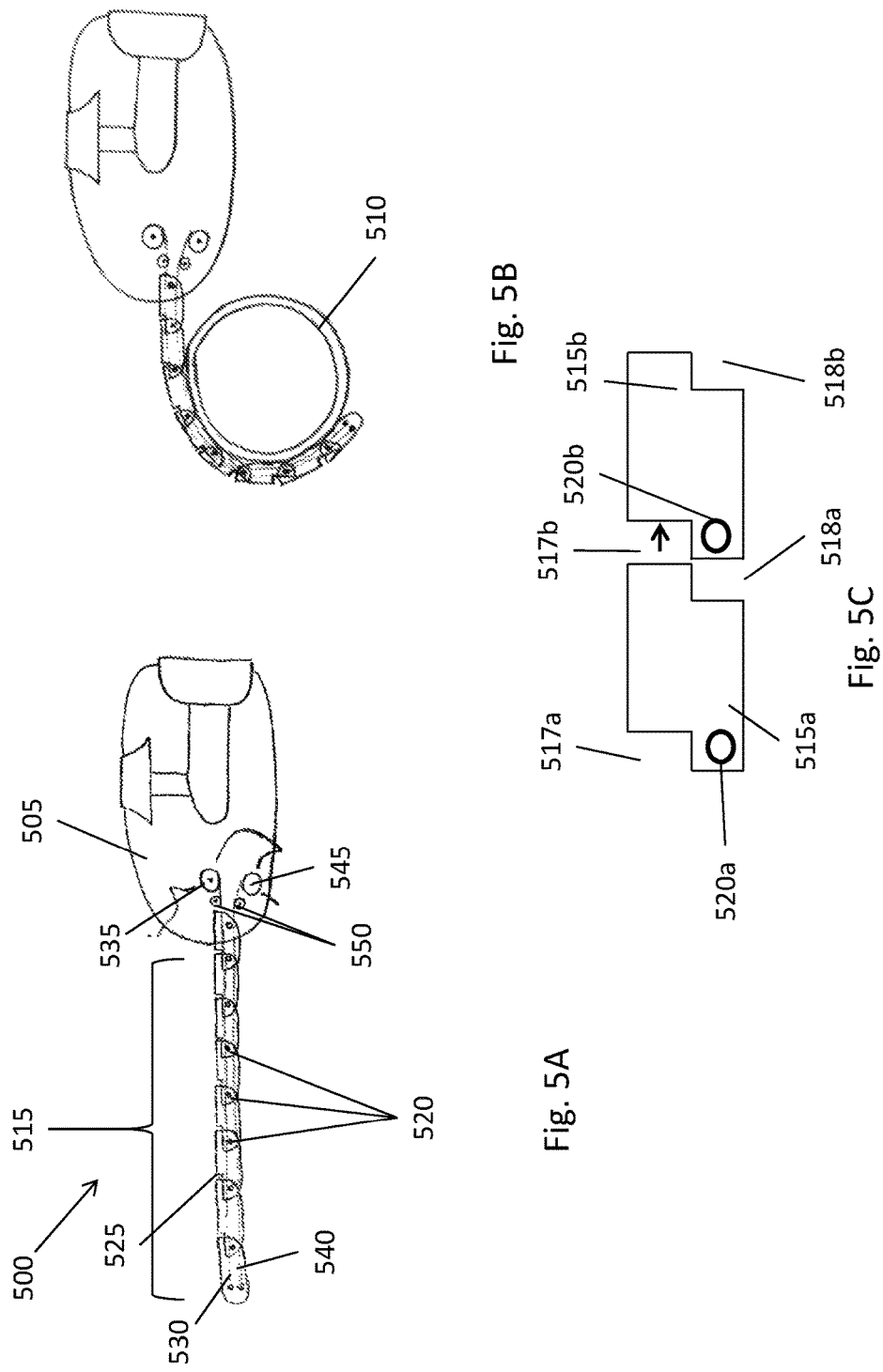

ATTACHMENT MECHANISMS FOR STABILZATION OF SUBSEA VEHICLES

CROSS-REFERENCE TO RELATED APPLICATIONS

This patent application claims the benefit of priority of U.S. Ser. No. 62/397,175, filed Sep. 20, 2016, entitled Underwater Vehicle Construction Operation, Coordination, and Control Attachments Therefor and Methods Relating to Same, which is hereby incorporated by reference as if set forth in its entirety herein.

FIELD OF THE INVENTION

This patent application relates to remotely operated vehicle inspection devices, and, more particularly, to mechanisms for securing remotely operated vehicles to subsea surfaces.

BACKGROUND

One common way to perform surface inspections of subsea structures such as pipelines, pilings, risers, and boat hulls is to navigate a remotely operated vehicle (ROV), such as by utilizing thruster jets, to the inspection surface, and to then deploy one or more robotic arms having inspecting tools therein. ROV-based inspections are particularly suitable for subsea pipelines that are vertically or horizontally installed in the ground, or suspended from a support structure.

It can be a challenge to maintain ROV stability during inspection, especially if the inspection surface is a structure suspended in water because such structures are less stable than seabed-implanted structures. Specifically, the challenge arises from reaction forces generated upon contact of inspection tools to the surface being inspected or cleaned. Since the ROV floats underwater, the ROV is particularly sensitive to such reaction forces due to buoyancy effects and the reaction forces can easily push the ROV backward to destabilize it. In particular, deploying cleaning jets, rotating brushes, and other marine life cleaning tools at an inspection surface imparts strong reaction forces to the ROV robotic arm, which leads to frequent destabilizations. Re-stabilizing the ROV or counteracting the reaction force can be accomplished by activating thrusters to provide a continuous thrust force in opposition to the reaction force. However, increased thruster use has several drawbacks. For instance, activating the thrusters depletes ROV battery power, thereby reducing ROV uptime. Constant re-stabilizing also agitates the seabed and churns the water, which reduces operator visibility, and introduces costly delays from continually having to reorient the robotic arm to the inspection surface.

As such, there exists a need for mechanical solutions to improve stabilization of ROVs during inspection and cleaning tasks without utilizing thrusters, in particular when such tasks are performed on pipelines. It is in regard to these issues that the present application is provided.

SUMMARY OF THE INVENTION

According to a broad aspect of the invention, attachment mechanisms for clamping a remotely operated vehicle to a subsea structure surface are provided.

In one aspect of the invention, embodiments of the attachment mechanism are suitable for securing a remotely operated vehicle (ROV) to a subsea structure. The attachment mechanism includes a motor for generating a rotational force. Further, the attachment mechanism includes a worm gear drive system driven by the motor, the worm gear system including a driveshaft, a worm screw, a wormshaft, a worm wheel, and a first pair of bevel gears. The driveshaft includes a first end and a second end, the first end coupled to the motor, and the worm screw is adjacent to the second end, the worm screw having a plurality of teeth disposed along its outer circumference and driven by the generated rotational force to rotate. The wormshaft includes the worm wheel disposed at a central portion of the wormshaft, the worm wheel being circumferentially throated to mesh with the plurality of teeth of the worm screw, such that when the worm screw is driven by the generated rotational force, the wormshaft rotates correspondingly. The first pair of bevel gears is coaxially disposed at each end of the wormshaft and the first pair of bevel gears bears a plurality of external teeth at their pitch surfaces.

Continuing with this aspect of the invention, embodiments of the attachment mechanism include a pair of grasping hooks, horizontally and vertically canted at an angle relative to operating orientation of the ROV in a mirrored orientation to one another, each grasping hook having a first end and a second end that is free. Additionally, the attachment mechanism includes a pair of hookshafts, a first end of each hookshaft being coupled to the first end of each grasping hook, the pair of hookshafts being oriented at an angle relative to the wormshaft. Moreover, a second pair of bevel gears is coaxial with and surrounding the pair of hookshafts and disposed adjacent to a second end of each hookshaft, the second pair of bevel gears bearing a plurality of external teeth at their pitch surfaces. In one or more embodiments, the attachment mechanism is arranged such that the external teeth of the first pair of bevel gears and the external teeth of the second pair of bevel gears mesh at a meshing angle, such that when the motor drives the worm gear system, the rotational force is transferred to the hookshafts to raise or lower the grasping hooks and to clamp the second end of the grasping hooks about the subsea structure.

In another aspect of the invention, embodiments of an attachment mechanism suitable for securing a remotely operated vehicle (ROV) to a subsea structure are provided. In one or more embodiments, the attachment mechanism includes a rigid holder having at first end mounted to the ROV and a second end that is free, the rigid holder having a mechanical stop disposed at the second end and a pivot point adjacent to the second end. Additionally, a swing arm is coupled to the rigid holder at the pivot point, the swing arm having a rolling element embedded therein and having a rest orientation. Further, a spring means is disposed between the mechanical stop and the swing arm, thereby providing a tension force to the swing arm. In one or more embodiments, the attachment mechanism is arranged such that upon contact to the subsea structure, a reaction force causes the swing arm to rotate inward toward the ROV until the tension force overcomes the reaction force, causing the swing arm to rotate to the rest orientation.

In another aspect of the invention, embodiments of an attachment mechanism suitable for securing a remotely operated vehicle (ROV) to a subsea structure are provided. In one or more embodiments, the attachment mechanism includes a plurality of linked segments connected in series by a plurality of pin joints disposed between each linked segment, the plurality of linked segments each having a mechanical stop configured to prevent the plurality of linked segments from rotating through a certain angle. Moreover, a flexible extension wire is connected to an extension pulley at one end and supported through the plurality of linked segments above the plurality of pin joints. Further, a flexible contraction wire is connected to a retraction pulley at one end and supported through the plurality of linked segments below the plurality of pin joints. The attachment mechanism additionally includes a first locking mechanism disposed at the extension wire and a second locking mechanism disposed at the retraction wire, the first and second locking mechanisms being configured to lock the plurality of linked segments in place by locking the extension wire and the contraction wire in place. In one or more embodiments, the attachment mechanism is arranged such that the extension pulley and the retraction pulley rotate to extend or retract the extension wire or retraction wire to actuate the plurality of linked segments.

In another aspect of the invention, a method of attaching a remotely operated vehicle to a subsea surface is provided. In one or more embodiments, the method implements a remotely operated vehicle initially in a rest orientation. The ROV is of a type having a rigid holder coupled to a swing arm with a rolling element embedded therein and a spring means disposed between the rigid holder and the swing arm. The method includes contacting a first portion of the surface of a subsea structure with a first face of the rolling element. The method advances the remotely operated vehicle in the direction of the subsea structure such that the first face of the rolling element contacts a second portion of the subsea structure and causes the swing arm to pivot toward the rigid holder and increase a tension force in the spring means. The remotely operated vehicle is then advanced in the direction of the subsea structure such that the first face of the rolling element passes an apex of the subsea structure and the tension force stored in the spring means is greater than a normal force exerted on the swing arm by the subsea structure. Further, the swing arm pivots away from the rigid holder back toward the rest orientation upon release of the tension force in the spring means. In some embodiments, the pivoting of the swing arm away from the rigid holder back toward the rest orientation causes the swing arm to contact a third portion of the subsea structure that is approximately diametrically opposed to the first portion of the subsea structure.

These and other aspects, features, and advantages of the invention can be further appreciated from certain embodiments of the invention described herein.

BRIEF DESCRIPTION OF THE DRAWINGS

The accompanying drawing figures illustrate exemplary embodiments and are not intended to be limiting of the invention. Among the drawing figures, like references are intended to refer to like or corresponding parts.

FIG. 4A illustrates a side view of the attachment mechanism of FIG. 3 during a securing operation to a subsea structure;

FIG. 4B illustrates a side view of the attachment mechanism of FIG. 3 during a continuation of the securing operation of FIG. 4A to a subsea structure;

FIG. 5A illustrates a side view of an attachment mechanism for securing a ROV to a subsea structure in accordance with an alternative embodiment of the present application;

FIG. 5B illustrates a side view of an attachment mechanism of FIG. 5B during a securing operation to a subsea structure; and FIG. 5C illustrates a side view of two exemplary linking segments of the attachment mechanism of FIGS. 5A and 5B.

DETAILED DESCRIPTION OF CERTAIN EMBODIMENTS OF THE INVENTION

Figure 1A:
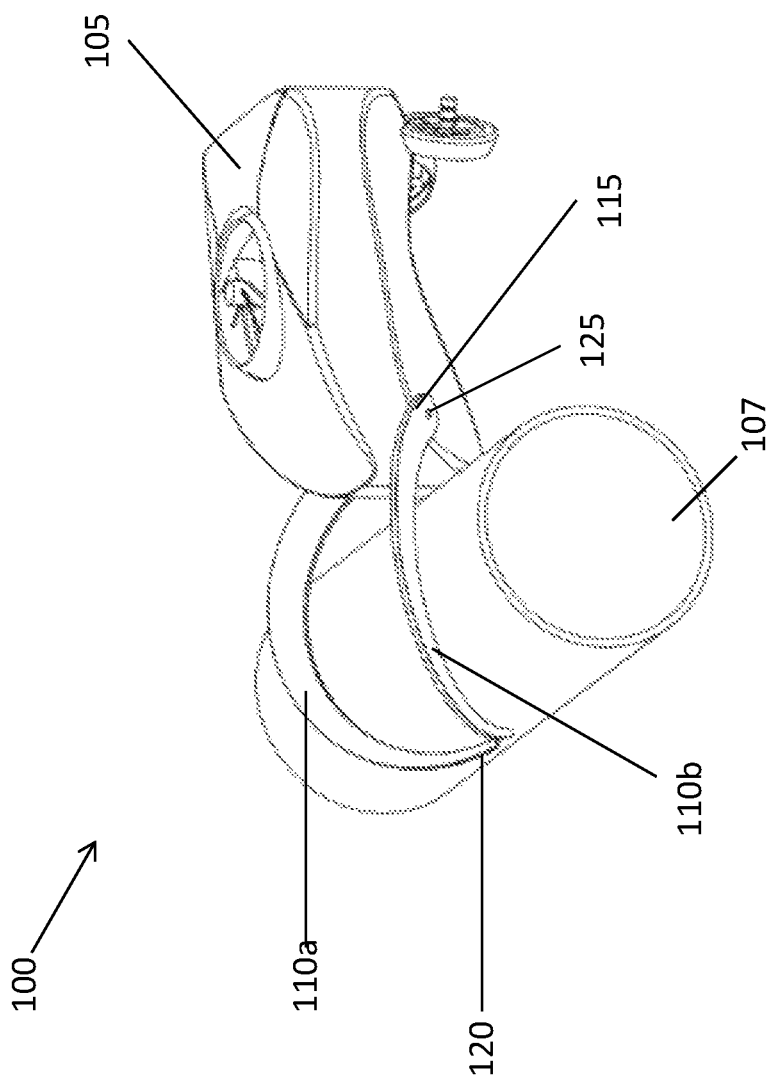
FIG. 1A illustrates a isometric side view of an attachment mechanism for securing a ROV to a horizontally oriented subsea structure in accordance with at least one embodiment of the present application.

In accordance with one or more aspects of the invention, embodiments are provided that are directed to attachment mechanisms to a robotic arm of a remotely operated vehicle (ROV) that improve ROV stability during subsea structure inspection and cleaning. In particular, the invention is described in connection with one or more embodiments in which the ROV is secured or clamped to the subsea structure to be inspected (e.g., a pipeline) by an attachment mechanism in such a way as to passively counteract destabilization of the ROV by reaction forces generated during inspection and cleaning activity. The provided attachment mechanisms use little to no power by latching to the subsea structure, thereby maintaining ROV stability with limited thruster utilization and, thus, preservation of battery life. Further, in one or more embodiments, the attachment mechanisms provided herein have a structure that is smaller in size than conventional clamping or other mechanisms such that the attachment mechanisms can be advantageously implemented by small, lightweight class ROVs, such as electric ROVs, general class ROVs, inspection class ROVs, observation class ROVs, and other battery operated ROVs of the type that do not use an umbilical cord to draw power from an above surface power source.

In one or more embodiments, the attachment mechanism is a motorized grasping type device in which one or more ambulatory grasping hooks extend from the front inspection-facing portion of the ROV. In one or more embodiments, the grasping hooks are configured to have a curved shape that engages a round or cylindrical subsea structure, such as a pipeline. The hooks are actuated from an open position to a closed position by an actuation system. In the open position, the ROV is not secured to the structure, whereas in the closed position the ROV is secured to the structure. In one or more embodiments, the actuation system comprises a motor, one or more bevel gears, and a worm gear drive system arranged to raise or lower the grasping hooks.

In one or more embodiments, the attachment mechanism comprises a rigid holder coupled to a rotatable swing arm designed to contact the subsea structure and adapt to the subsea structure surface until secured in place by a mechanical stop. The swing arm comprises a rolling element, such as one or more rollers. The swing arm is coupled to the rigid arm at a pivot point and by a spring means disposed between the swing arm and the mechanical stop. The mechanical stop restricts the rotation of the surface arm in one direction.

In one or more embodiments, the attachment mechanism comprises a plurality of linked segments, connected in series to one another by a pin joint. The pin joint and the shape of the linked segments function as a mechanical stop, such that plurality of linked segments can rotate inwards in a finger-like movement, but cannot extend much beyond a straight, horizontal extension.

The invention is now described with reference to the accompanying drawings, which form a part hereof, and which show, by way of illustration, example implementations and/or embodiments of the present invention. It is to be understood that other embodiments can be implemented and structural changes can be made without departing from the spirit of the present invention. Among other things, for example, the disclosed subject matter can be embodied as methods, devices, components, or systems.

Furthermore, it is recognized that terms may have nuanced meanings that are suggested or implied in context beyond an explicitly stated meaning. Likewise, the phrase "in one embodiment" as used herein does not necessarily refer to the same embodiment and the phrase "in another embodiment" as used herein does not necessarily refer to a different embodiment. It is intended, for example, that claimed subject matter can be based upon combinations of individual example embodiments, or combinations of parts of individual example embodiments.

Figure 1B:
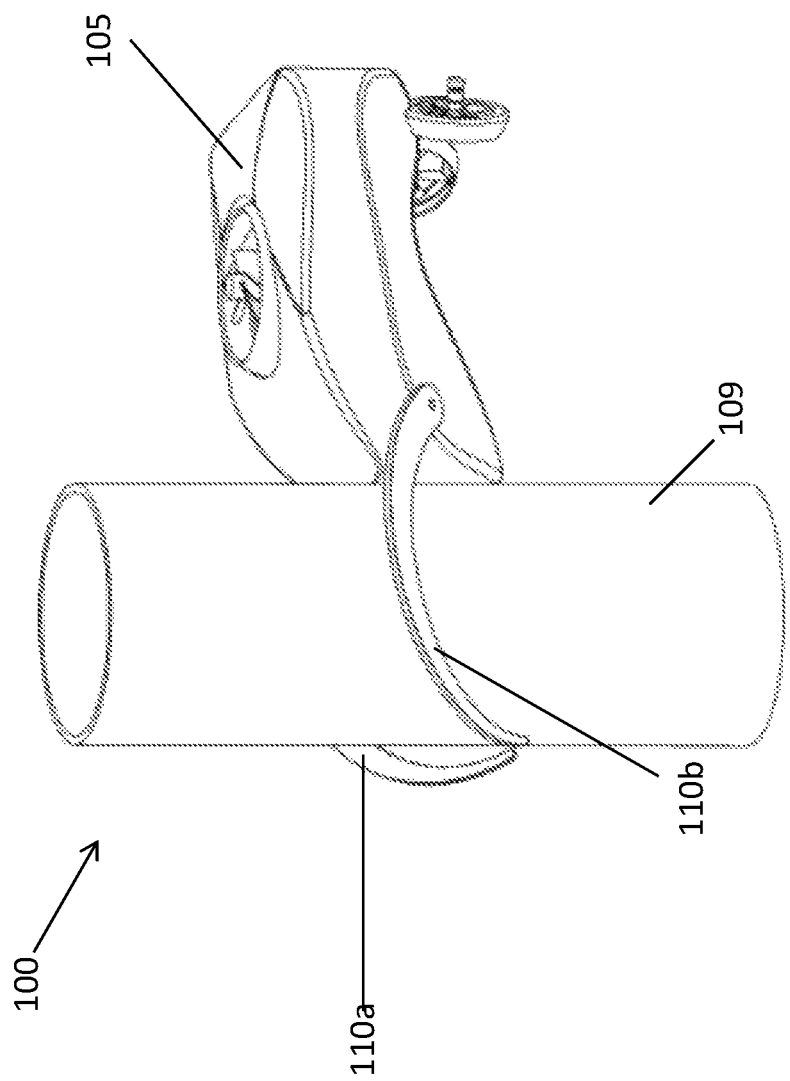
FIG. 1B illustrates an isometric side view of the attachment mechanism of FIG. 1A as secured to a vertically oriented subsea structure.

With reference now to FIGS. 1A and 1B, an attachment mechanism 100 for securing a ROV to a subsea structure in accordance with at least one embodiment of the present application is provided. In one or more embodiments, the attachment mechanism 100 is coupled to a ROV 105 so as to comprise an accessory for the ROV. Coupling to the ROV can be in any conventional way, such as by bolts. Advantageously, the attachment mechanism 100 can be attached to small, lightweight ROVs such as electric ROVs, general class ROVs, inspection class ROVs, observation class ROVs, and other battery operated ROVs. In the exemplary embodiment, the attachment mechanism 100 is designed to surround and clamp the ROV to a cylindrical pipeline (e.g., horizontal pipeline 107, as shown in FIG. 1A; vertical pipeline 109, as shown in FIG. 1B), though the attachment mechanism can be configured to clamp to other subsea surfaces such as pilings, or hulls, and can be suitably configured for clamping to target objects of arbitrary shape.

In one or more embodiments, the attachment mechanism 100 includes a pair of grasping hooks 110a, 110b (or "curved members"). The grasping hooks 110 include a first or upper end 115 and a second, or lower free end 120. In one or more embodiments, the grasping hooks 110 extend from each of their first ends 115 to their second ends 120 along a circular arc of at least 180° so as to cooperate with the abutment point of the attachment mechanism 100 to the ROV 105 in such a way as to generally surround and clamp to the pipe 107, at least along one side of the pipe as illustrated in FIG. 1A. In the exemplary embodiment illustrated by FIGS. 1A and 1B, the pair of grasping hooks 110a, 110b are canted both in horizontal and vertical planes relative to the operating orientation of the ROV. Advantageously, forming the grasping hooks with a cant or tilt allows the attachment mechanism 100 to secure the ROV 105 to both horizontally and vertically oriented subsea structures without needing to reorient the ROV or any attachment arms. This is because the tilt of the grasping hooks 110 allows different portions of the hooks to attach to a subsea structure. For example, as shown in FIG. 1A, the underside of each grasping hook 110 encircles the curvature of a horizontally oriented pipe 107. Then, as illustrated by FIG. 1B, the ROV 105 can attach to a vertically oriented pipe 109 by encircling the pipe with the inside edges of the grasping hooks 110. Attaching to either a horizontally oriented pipe 107 or a vertically oriented pipe 109 is thereby accomplished without changing the orientation of the ROV. Advantageously, this reduces ROV 105 thruster use, which is desirable for smaller, lightweight ROVs. Additionally, approaching at an angle ensures that the grasping hooks 110 wrap around a subsea structure in a tighter fashion than if the hooks were to be mounted orthogonal to the pipe.

In one or more embodiments, the tilted orientations of the first hook 110a and the second hook 110b are such that the orientation of the pair of grasping hooks is mirrored. For example, if the first hook 110a is tilted 45 degrees from both the horizontal and the vertical planes, the second hook 110b is tilted negative 45 degrees from both the horizontal and the vertical planes. In a particular embodiment, the grasping hooks 110 are formed with a cant or tilt of 45 degrees. This angle provides the most versatility for the ROV to grasp onto both horizontal and vertical pipes (e.g., pipelines 107, 109), though in practice, the cant or tilt of the grasping hooks 110 can vary a small amount (e.g., +/−5 degrees) from 45 degrees and is still effective in securing the ROV 105 to both horizontal and vertical oriented cylindrical surfaces.

Figure 2:
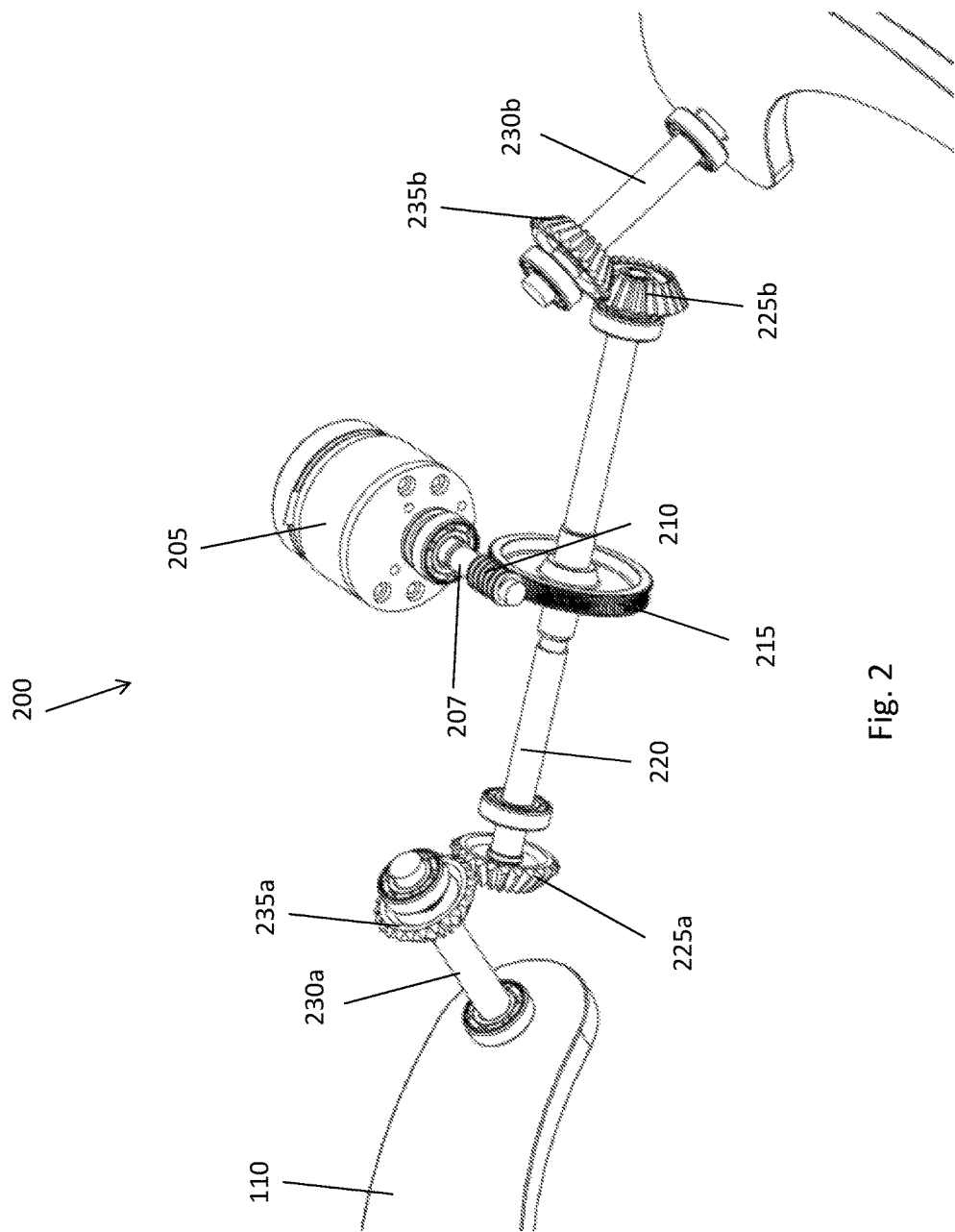
FIG. 2 illustrates a schematic view of an actuation system for an attachment mechanism in accordance with at least one embodiment of the present application.

With reference now to FIGS. 1A, 1B and 2, the grasping hooks 110 are mechanically coupled to a worm gear drive system 200 housed with ROV 105. The worm gear drive system 200 is a motorized arrangement of gears and shaft components that when driven, serves to actuate the grasping hooks 110 to pivot upwardly and downwardly in a vertical plane in an arc to facilitate engagement with the subsea surface e.g., horizontal pipeline 107, vertical pipeline 109) and secure the ROV 105 in place during inspection of the subsea surface. In one or more embodiments, the worm gear drive system 200 includes a motor 205 that drives an enmeshed worm screw 210 and worm wheel 215 combination (a "worm gear") to rotate an elongated wormshaft 220 having a first pair of bevel gears 225a, 225b (and more generally bevel gears 225) disposed at each end. In this way, torque amplification is provided to the wormshaft 220. The worm wheel 215, in one or more embodiments, is disposed about the circumference of and coaxially with the wormshaft 220. In one or more embodiments, the worm wheel 215 is located at the center of the wormshaft 220. One or more bearings can be included about the circumference of the wormshaft 220. For example, a bearing can be positioned adjacent to each of the bevel gears 225a, 225b. The bevel gears 225 are designed to have a pitch angle of less than 90 degrees and to engage with a similarly pitch angled second pair of bevel gears 235a, 235b (and more generally bevel gears 235) that are disposed at an end of a hook shaft 230, The hook shaft 230 is coupled to the grasping hooks 110 and thus, when driven by the motor, this sequence of mechanical engagements serves to raise or lower the grasping hooks 110.

It can be appreciated that while the illustrated embodiments and discussion herein refer to "pairs" of hooks, hookshafts, and bevel gears, the advantages of having more than one hook and corresponding hookshaft and bevel gear extend more generally to a "set" of hooks, hookshafts and bevel gears. As such, each of the embodiments described herein can more generally be constructed so as to have a set of hooks each with a respective hookshaft and engaged to a bevel gear, wherein the set comprises from one to many hooks and hookshafts and possibly many bevel gears.

More particularly, as shown in the exemplary embodiment in FIG. 2, the worm gear drive system 200 includes a motor 205 that drives a driveshaft 207 that is coupled to the motor at a first end. One or more bearings can be implemented adjacent to the first end of the driveshaft 207 to facilitate coupling the driveshaft to the motor 205. The dtiveshaft 207 is a cylindrical shaft having a portion fashioned into a worm screw 210 adjacent to the second end of the driveshaft 207. As the motor 205 drives the driveshaft 207, the driveshaft rotates either clockwise or counter-clockwise about its longitudinal axis. The worm screw 210 then transfers this rotational motion to a worm wheel 215 that is meshed with the worm screw.

As shown by FIG. 2, the worm wheel 215 is positioned perpendicular to and meshed with the worm screw 210 to encompass a worm gear, such that the rotational motion generated by the motor 205 to the worm screw and transferred to the worm wheel causes the worm wheel to rotate clockwise or counter-clockwise about the horizontal longitudinal axis of the wormshaft 220. This in turn causes the wormshaft 220 to rotate about its horizontal longitudinal axis. To facilitate meshing of the worm gear, the worm screw and the worm wheel can include a plurality of teeth and grooves machined along their outer circumferences that are sized and shaped to correspondingly couple the worm screw and the worm wheel. The worm gear can be non-throated (i.e., no grooves machined around the circumference of the worm screw 210 or worm wheel 215), single-throated (i.e., grooves are machined around the circumference the worm wheel 215), or double-throated (i.e., grooves are machined around both the circumference of the worm screw 210 and the worm wheel 215). In one or more embodiments, the worm wheel 215 is throated to include a plurality of teeth disposed along its outer circumference that are sized and shaped to engage with a throated worm screw 210.

A first pair of bevel gears 225a, 225b bearing a plurality of external teeth at their pitch surfaces are disposed coaxially with, and at, each end of the wormshaft 220. In one or more embodiments, the bevel gears 225 are mounted to provide a particular pitch angle. For example, in one embodiment, the bevel gears 225 have a pitch angle of 22.5 degrees, though other pitch angles can be contemplated depending on the desired range of motion for the attachment mechanism 100.

In one or more embodiments, the worm gear drive system 200 generates a rotational force that serves to pivot the grasping hooks 110 of the attachment mechanism 100 in an upward or downward motion, thereby securing the ROV 105 to a subsea surface, Advantageously, the torque amplification effects provided by worm gear drive system 200 serve as a locking mechanism against inadvertent grasping hook 110 motions. More simply, due to the meshing nature of the first bevel gears 225 and the second bevel gears 235, without the torque amplification provided by the motor 205, the grasping hooks 110 are held in place. The bevel gears are selected such that during typical use, external forces, such as those generated by the ROV or the grasping hooks 110 during contact with a surface, do not exceed the torque amplification threshold necessary to rotate the bevel gears.

To effect grasping hook 110 actuation by the worm gear drive system 200, in one or more embodiments, the first end 115 of the grasping hooks 110 defines an aperture or cavity 125 for receiving a first end of a pair of hook shafts 230a, 230b that couple the first end 115 to the ROV 105. In one or more embodiments, the grasping hooks 110 are coupled to the worm gear drive system 200 at the first end 115 via a pin, screw, epoxy, adhesive or other fastener. Each of a second pair of bevel gears 235, bearing a plurality of external teeth at their pitch surfaces, surround each of the hook shafts 230a, 230b and are disposed at or adjacent to, and coaxial with, a second end of each hook shaft 230. The first pair of bevel gears 225 and the second pair of bevel gears 235 are correspondingly throated (i.e., having grooves sized and shaped to mesh with the plurality of teeth disposed about the circumference of other gears) such that as the first pair of bevel gears rotate, the meshed second pair of bevel gears receive the rotational force and rotate in the opposite direction due to the meshing. This meshing compels the hook shafts 230 to rotate and thereby raise or lower the grasping hooks 110. For example, the teeth of bevel gear 225a mesh into the grooves of bevel gear 235a, and vice versa.

The arc range of motion of the grasping hooks 110 can be varied depending on the particular angles (the "meshing angle") that the bevel gears 225 have relative to the bevel gears 235 when the two gear sets mesh. The meshing angle is calculated by summing the respective pitch angles of the bevel gears. For example, the exemplary embodiment in FIG. 2 has a meshing angle of 45 degrees created by the first pair of bevel gears 225 and the second pair of bevel gears 235 both having pitch angles of 22.5 degrees. Other gear meshing angles can be implemented by implementing bevel gears having different pitch angles, such as 15, 30, 60, 75, or 90 degrees, depending on the desired range of motion for the attachment mechanism 100. Further, in one or more embodiments, the bevel gears 235 have the same or similar size and throated configuration as the bevel gears 225. Each of the bevel gears is not required to be an identical size, as, for example, larger or smaller bevel gears 235 can be implemented in order to compensate for a larger or smaller meshing angle.

Many subsea surfaces, such as pipelines, have ferromagnetic properties. To increase adherence to the inspection surface, in one or more embodiments, magnetic material can be embedded in the grasping hooks 110 at or adjacent to the first free end. The magnetic material can be made of iron, nickel, cobalt, rare earth metals, and alloys thereof.

Subsea surfaces also can also be covered in protective coating, such as for cathodically protected pipelines. In one or more embodiments, the grasping hooks 110 are covered with a rubber coating for preventing subsea structure damage when the hooks clamp onto the structure. In one or more embodiments, protective padding or cushion is fixed to the front surface of the ROV 105 that is between the coupled first ends 115 of the grasping hooks 110 such that if the ROV contacts the structure surface, no or little damage is done to the surface. In one or more embodiments, a rolling element is fixed to the underside of the grasping hooks and/or the front surface of the ROV 105 between the coupled first ends 115. For example, the rolling element can include one or more rollers, ball bearings, or wheels such that when the ROV 105 is clamped to the surface, if the ROV activates thrusters, the grasping hooks 110 and/or ROV body rolls across the structure circumferentially. This provides an additional degree of freedom (i.e., a pitch angle) that allows for more effective cleaning and inspection methods.

Figure 3:
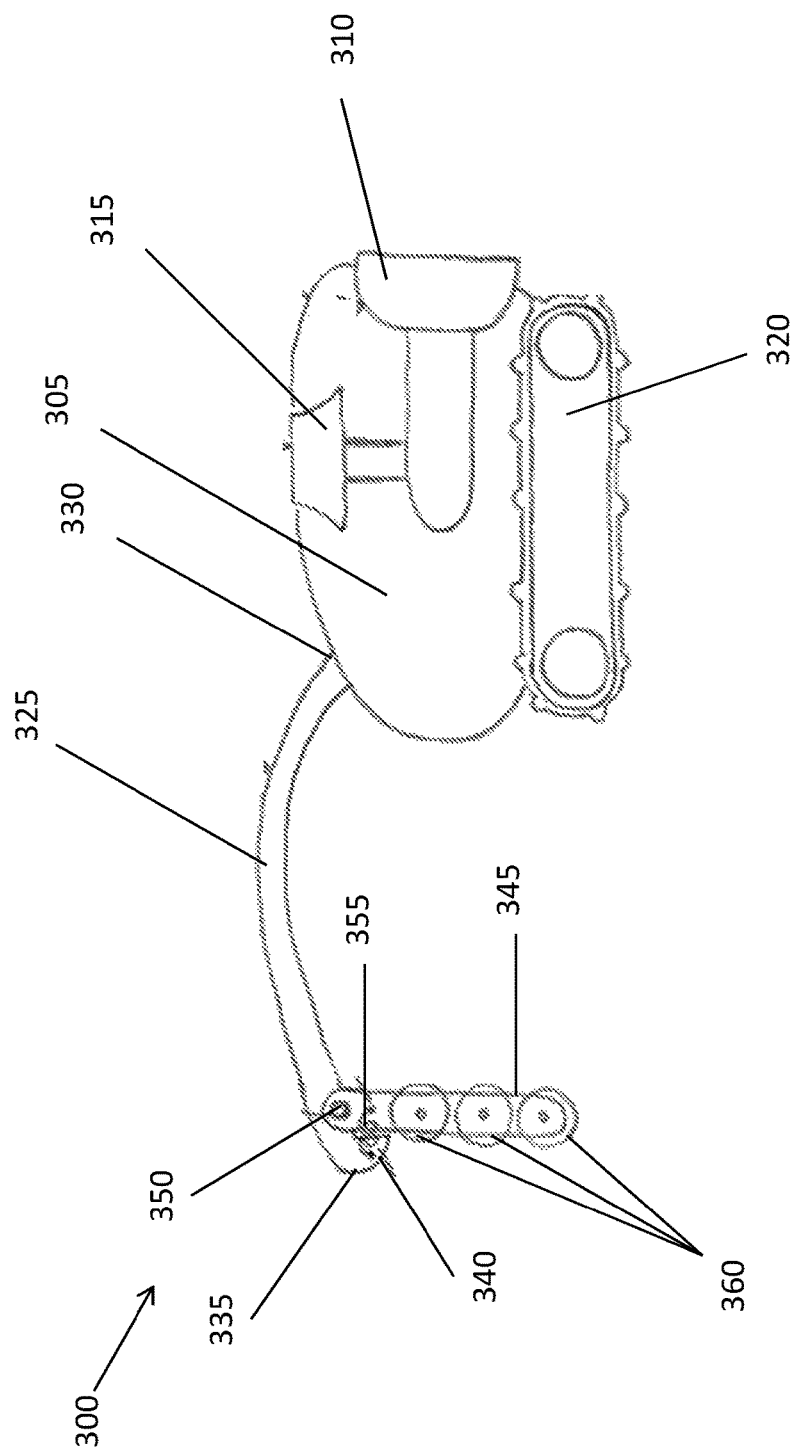
FIG. 3 illustrates a side view of an attachment mechanism for securing a ROV to a subsea structure in accordance with an alternative embodiment of the present application.

With reference now to FIG. 3, an attachment mechanism 300 for securing a ROV to a subsea structure in accordance with at least one embodiment of the present application is provided. If the subsea structure to be inspected or cleaned is embedded in the earth or situated on the seabed, a negatively buoyant ROV 305 can be implemented. Negatively buoyant ROVs primarily operate by crawling along the seabed using treads or wheels. While attachment mechanism 300 is advantageously implementable with negatively buoyant ROVs, the attachment mechanism 300 according to one or more embodiments herein can be used with other traditional ROVs (e.g., ROV 105). ROV 305 includes horizontal thrusters 310 and vertical thrusters 315 for navigating to and along the seabed. However, once on the seabed, thruster utilization is preferably minimized by employing motorized treads 320 as the primary means for moving along the seabed, as thruster utilization on the seabed can agitate the seabed by stirring up loose, soft sand, thereby limiting operator visibility of the environment.

Attachment mechanism 300 includes a rigid holder 325 having a first or attachment end 330 that is mounted at the front surface of the ROV 305. In one or more embodiments, the rigid holder 325 extends from its first end to a second end 335 along a circular arc of up to 180 degrees (as illustrated). In other embodiments, the rigid holder 325 extends in a straight line without a bend. The leading surface of the second end 335 can be shaped into a rounded or other aerodynamic head to facilitate passing through the water with minimized friction. In one or more embodiments, the second end 335 includes a mechanical stop 340. For example, the mechanical stop 340 can be a portion of the second end 335 that extends downwardly from the longitudinal span of rigid holder 335 to define a lip, the lip having an underside surface that is oppositely facing from the leading surface of the second end. The mechanical stop 340 can also include other flanges, blocks, or impediments.

In one or more embodiments, the attachment mechanism 300 includes a spring loaded swing arm 345 coupled to the rigid holder 325 at a pivot point 350 about which the swing arm can rotate. The pivot point 350 is disposed adjacent to the second end 335 at a point near the mechanical stop 340 such that at rest, the swing arm 345 hangs substantially perpendicular to the seabed in a rest position. A spring means 355 is disposed between the mechanical stop 340 and the swing arm 350. The spring means 355 provides a spring force that urges the swing arm 345 toward the mechanical stop 340. For example, if the mechanical stop 340 defines a lip as shown in FIG. 3, the spring means 355 is fixed to the underside of that lip and biased to maintain the swing arm 345 rest position orientation relative to the rigid holder 325. The spring means 355 can be a compression spring, tension spring, or other known spring means. In one or more embodiments, a freely rotatable rolling element 360 is embedded in the swing arm 345. The rolling element 360 can include one or more rollers, ball bearings, wheels, and the like.

The operation of attachment mechanism 300 is illustrated by FIGS. 4A-4B. As shown in FIG. 4A, the thrusters 310, 315 and/or motorized tread 320 actuate the ROV 305 to bring it into proximity with a subsea structure 405 to be cleaned or inspected until the swing arm 345 contacts a first portion of the structure. As the ROV 305 continues to advance toward the subsea structure 405, such that the rolling element 360 of the swing arm 345 moves across the subsea structure surface to a second portion of that surface, a reaction force is generated. The reaction force urges the swing arm 345 to pivot inward toward the rigid holder 325 of the ROV 305 about the pivot point 350. As the swing arm 345 pivots, the spring means 355 stretches and extends to provide a spring tension force that urges the swing arm downward toward the outer surface of the subsea structure 405, causing the swing arm to continue to abut the outer surface as the ROV 305 moves forward. During pivoting, the rolling element 360 facilitates the circumferential sliding of the swing arm 345 along the outer surface of subsea structure 405. In this way, the rolling element 360 provides an additional degree of freedom in the pitch angle plane.

When the ROV 305 moves forward enough such that the free end of the swing arm 345 passes by the apex of the subsea structure 405, the spring tension force provided by the spring means 355 overcomes the reaction force and frictional surface forces from the subsea structure to pivot the swing arm back toward the mechanical stop 340 in the rest position, as illustrated by FIG. 4B. The mechanical stop 340 then prevents further outward rotation. In this way, the swing arm 345 serves to embrace the subsea structure 405 and hold the ROV 305 in place. In one or more embodiments, the ROV 305 embraces the subsea structure 405 by the swing arm 345 contacting a third portion of the subsea structure 405, in which the third portion is approximately diametric to the first portion of the subsea structure. Thereafter, the ROV 305 can perform cleaning and inspection tasks using, for example, cleaning nozzles, inspection arms, and other tools (not shown) while compensating for reaction forces created by performing such tasks. To further counteract reaction forces, an additional rolling element (that can be the same or similar to rolling element 360) can be fixed to the front surface of the ROV 305 below the rigid holder 325, such that when the swing arm 345 is in the clamped position as in FIG. 4B, the vertical thrusters 315 can be utilized to further facilitate the attachment mechanism 300 sliding across the subsea structure. In one or more embodiments, protective padding or cushioning is fixed to the front surface of the ROV 305 below the rigid holder 325 such that if the ROV contacts the subsea structure 405 surface, no or little damage is done to the surface or the ROV.

As will be appreciated, the swing arm 345 has a length that is selected in view of the overall distance that the rigid holder 325 displaces the pivot 350 from the attachment point 330 to the rover 305, and in further view of the anticipated diameter (or other dimension) of the object to be grasped, such as the subsea structure 405. As illustrated in FIGS. 4A and 4B, the swing arm pivots in response to forces imparted by the subsea structure 405 to an upward position and returns to its rest position (FIG. 4B) after the rover 305 has advanced leftward in the figures until the subsea structure 405 is proximate the forward end of the rover. Thereafter, the rover can move in reverse to bring the swing arm 345 into sure contact with the subsea structure (namely, the left side of the subsea structure, as illustrated).

With reference now to FIGS. 5A-C, an attachment mechanism 500 for securing a ROV to a subsea structure in accordance with at least one embodiment of the present application is provided. The attachment mechanism 500 is coupled to a ROV 505 in the same or similar way as attachment mechanism embodiments are coupled ROV 105 or ROV 305 above, and, as described below, is driven by a mechanism within the ROV to provide its attachment functionality. The attachment mechanism 500 is configured to provide a finger-like clamping mechanism that enables the ROV 505 to clamp to a variety of subsea structures (e.g., subsea structure 510, illustrated as a pipeline in FIG. 5B) having various geometries and diameters, and without implementing thrusters as a part of the attachment mechanism. During operation, the attachment mechanism 500 has an extended or unclamped state, as shown by FIG. 5A, in which a plurality of linked segments 515 are horizontally coaxially aligned in series. As the ROV 505 approaches a subsea structure 510, preferably from above the structure, as shown by FIG. 5B, the plurality of linked segments 515 are actuated to curl about the outer surface of the subsea structure and clamp the ROV in place during cleaning or inspection (a "clamped state"). To facilitate clamping, in one or more embodiments, the plurality of linked segments 515 can be coated in rubber material to increase the grip friction and reduce scraping at a subsea structure surface. In one or more embodiments, magnets or electromagnets can be disposed within and adjacent to the lower surface of the linked segments 515 help stabilize the attachment mechanism 500 to the subsea structure surface.

More particularly, the plurality of linked segments 515 are coupled at a plurality of pin joints 520, with a pin joint between each two linked segments. The linked segments 515 are machined so that each defines a mechanical stop 525 at the upper surface of a given segment. For example, as shown in FIG. 5C, the plurality of linked segments 515*a*, 515*b* can be machined to define a pair of corresponding notches 517, 518 that enable each segment to be seated in the segment that follows it, thereby functioning as a mechanical stop 525. In one embodiment, a first rectangular notch 517*a* is disposed at the upper left portion of the linking segment 515*a* and a second rectangular notch 518*a* is disposed at the lower right portion of linking segment 515*a*. In this way, the linking segment 515*a* is S-shaped, though the upper and lower surfaces can be rounded or concave to adapt to the outer surface of a subsea structure 510. As can be seen, the upper right portion of linking segment 515*a* can be seated in the first notch 517*b* of the linking segment 515*b*, which is the next linking segment, whereas the lower left portion of the linking segment 515*b* is seated in second notch 518*a* of the linking segment 515*a*. The two linking segments 515*a*, 515*b* are then coupled at a pin joint 520*b*. This arrangement provides a mechanical stop 525 that allows linking segment 515*a* to rotate downward to a certain angle (e.g.,5, 10, or 15 degrees), but the first notch 517 prevents upward rotation of the plurality of linking segments beyond approximately the zero degree level horizontal plane (i.e., substantially straight). This linking arrangement continues for each of the plurality of linking segments 515, except for the first linking segment (which in some arrangements, does not include a first notch 517, as nothing links to the front of it), and the last linking segment (which in some arrangements, does not include a second notch 518, as that portion of the linking segment can be coupled to the ROV 505). Further, each linking segment 515 in one or more embodiments is preferably identical to all the others (except the first and last segment as above), although they could differ in construction. In this way, linking segments 515 can be added or removed to increase or decrease the length of the attachment mechanism 500 needed to clean or inspect the subsea structure 510.

As buoyancy, current, and gravitational effects are inherent in a subsea environment, the attachment mechanism 500 needs to be actuated to operate from the unclamped to the clamped state by an actuation mechanism. In one or more embodiments, to control the clamping operation, the actuation mechanism includes an extension wire 530 connected to an extension pulley 535, and a retraction wire 540 connected to a retraction pulley 545. The extension wire 530 and the retraction wire 540 are flexible wires or cables that are supported within the plurality of linking segments 515 and terminate at one end within the first linking component, and terminate at the pulleys that are housed within the ROV 505 at the other end. In one or more embodiments, the extension wire 530 is supported above the plurality of pin joints 520, and the retraction wire 540 is supported below the pin joints.

The extension pulley 535 and the retraction pulley 545 are housed within the ROV 505 and can be motorized or spring loaded pulleys for actuation, and are configured for synchronized rotation, though in opposite directions (i.e., if the extension pulley rotates clockwise, the retraction pulley rotates counter-clockwise). Both the extension wire 530 and the retraction wire 540 are made of materials capable of bending upwards and downwards. Thus, during actuation of the extension pulley 535 and retraction pulley 545 via a motor or by releasing or compressing a spring force, the wires extend or retract correspondingly into the ROV 505 around the respective connected pulley, thereby rotating the plurality of linked segments 515 inward or outward.

In one or more embodiments, the attachment mechanism 500 includes one or more locking mechanisms 550 in connection with the extension wire 530 and/or the retraction wire 540 for limiting pulley motor power consumption during clamping operation. The locking mechanism 550 limits power consumption by locking the extension wire 530 and retraction wire 540 in place during surface cleaning or inspection, without requiring a motor to continually drive the extension pulley 535 and retraction pulley 545 to maintain contact between the plurality of linking segments 515 and the surface, as reaction forces are generated by cleaning or inspection. The locking mechanisms 550 are typically housed within the ROV 505 adjacent to the extension pulley 535 and retraction pulley 545, though the locking mechanism could be arranged within the plurality of linking segments 515 so long as it can serve to communicate with the pulley motor(s). In some arrangements, a single locking mechanism 550 is housed within the ROV 505 between the extension wire 530 and retraction wire 540. In other arrangements, a first locking mechanism is housed in the ROV 505 below and in connection with the extension wire 530, and a second locking mechanism is housed in the ROV above and in connection with the retraction wire 540.

While the exemplary embodiment shown in FIGS. 5A-C contemplates rotating the attachment mechanism downward to adhere to a subsea surface, in one or more embodiments, the actuation mechanism can include additional motors, wires, and pulleys arranged in a similar way as provided above to introduce addition clamping angles. For example, an additional motor/wire/pulley system can be arranged to provide sideways or a slight upward movement to the plurality of linked segments 515. Such upward movement can comprise angles 0-15 degrees from the horizontal plane of the linked segments 515 at a level orientation. In this way, the attachment mechanism 500 can be adapted to clamp to vertically oriented structures and other structure orientations.

Notably, the figures and examples above are not meant to limit the scope of the present application to a single implementation, as other implementations are possible by way of interchange of some or all of the described or illustrated elements. Moreover, where certain elements of the present application can be partially or fully implemented using known components, only those portions of such known components that are necessary for an understanding of the present application are described, and detailed descriptions of other portions of such known components are omitted so as not to obscure the application. In the present specification, an implementation showing a singular component should not necessarily be limited to other implementations including a plurality of the same component, and vice-versa, unless explicitly stated otherwise herein. Moreover, applicants do not intend for any term in the specification or claims to be ascribed an uncommon or special meaning unless explicitly set forth as such. Further, the present application encompasses present and future known equivalents to the known components referred to herein by way of illustration.

The foregoing description of the specific implementations will so fully reveal the general nature of the application that others can, by applying knowledge within the skill of the relevant art(s) (including the contents of the documents cited and incorporated by reference herein), readily modify and/or adapt for various applications such specific implementations, without undue experimentation, without departing from the general concept of the present application. Such adaptations and modifications are therefore intended to be within the meaning and range of equivalents of the disclosed implementations, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various implementations of the present application have been described above, it should be understood that they have been presented by way of example, and not limitation. It would be apparent to one skilled in the relevant art(s) that various changes in form and detail could be made therein without departing from the spirit and scope of the application. Thus, the present application should not be limited by any of the above-described example implementations.

What is claimed:

1. An attachment mechanism suitable for securing a remotely operated vehicle (ROV) to a subsea structure, comprising:
    a rigid holder having at first end mounted to the ROV and a second end that is free, the rigid holder having a mechanical stop disposed at the second end and a pivot point adjacent to the second end;
    a swing arm coupled to the rigid holder at the pivot point, the swing arm having a rolling element embedded therein and in a rest orientation; and
    a spring means disposed between the mechanical stop and the swing arm, thereby providing a tension force to the swing arm,
    wherein the swing arm is configured to rotate inward toward the ROV and away from the rest orientation until the tension force overcomes a reaction force generated from contact with the subsea structure to return the swing arm to the rest orientation.

2. The attachment mechanism of claim 1, wherein the rigid holder extends from its first end to the second end along a circular arc of 0 to 180 degrees.

3. The attachment mechanism of claim 1, wherein the mechanical stop includes a lip, the lip having an underside surface that is opposite to a leading surface of the second end that the swing arm cannot rotate beyond.

4. The attachment mechanism according to claim 1, wherein the rigid holder extends from its first end to the second end without a bend.

5. The attachment mechanism according to claim 1, wherein the second end of the rigid holder is rounded.

6. The attachment mechanism according to claim 1, wherein the mechanical stop includes one or more flanges.

7. The attachment mechanism according to claim 1, wherein the rest orientation orients the swing arm substantially perpendicular to a seabed.

8. The attachment mechanism according to claim 1, wherein the spring means is a compression spring.

9. The attachment mechanism according to claim 1, wherein the spring means is a tension spring.

10. The attachment mechanism according to claim 1, wherein the rolling element includes one or more rollers, one or more ball bearings, or one or more wheels.

11. A method of attaching a remotely operated vehicle to a surface of a subsea structure, the remotely operated vehicle initially in a rest orientation, the remotely operated vehicle being of the type having a rigid holder coupled to a swing arm with a rolling element embedded therein and a spring means disposed between the rigid holder and the swing arm, the method comprising:
    contacting a first portion of the subsea structure with a first face of the rolling element;
    advancing the remotely operated vehicle in the direction of the subsea structure such that the first face of the rolling element contacts a second portion of the subsea structure and generates a reaction force that causes the swing arm to pivot toward the rigid holder and increase a tension force in the spring means;
    advancing the remotely operated vehicle in the direction of the subsea structure such that the first face of the rolling element passes an apex of the subsea structure and the tension force stored in the spring means is greater than the reaction force exerted on the swing arm; and
    pivoting the swing arm away from the rigid holder back toward the rest orientation by releasing the tension force in the spring means.

12. The method according to claim 11, wherein pivoting the swing arm away from the rigid holder back toward the rest orientation causes the swing arm to contact a third portion of the subsea structure that is approximately diametric to the first portion of the subsea structure.

13. The method according to claim 11, wherein the steps of advancing the remotely operated vehicle further comprise activating one or more horizontal thrusters.

14. The method according to claim 11, wherein the steps of advancing the remotely operated vehicle further comprise activating one or more vertical thrusters.

15. The method according to claim 11, wherein the steps of advancing the remotely operated vehicle further comprise activating one or more motorized treads.

* * * * *